US012569559B1

(12) United States Patent
Xu

(10) Patent No.: US 12,569,559 B1
(45) Date of Patent: Mar. 10, 2026

(54) ENGINEERED DENDRITIC CELL AND USE THEREOF

(71) Applicant: InmuCell Therapy (US) INC., San Diego, CA (US)

(72) Inventor: Yang Xu, San Diego, CA (US)

(73) Assignee: InmuCell Therapy (US) INC., San Diego, CA (US)

( * ) Notice: Subject to any disclaimer, the term of this patent is extended or adjusted under 35 U.S.C. 154(b) by 0 days.

(21) Appl. No.: 19/031,443

(22) Filed: Jan. 18, 2025

(51) Int. Cl.
| | |
|---|---|
| *A61K 40/42* | (2025.01) |
| *A61K 40/19* | (2025.01) |
| *A61K 40/31* | (2025.01) |
| *A61P 35/00* | (2006.01) |
| *C07K 14/725* | (2006.01) |
| *C07K 16/28* | (2006.01) |

(52) U.S. Cl.
CPC ............ *A61K 40/422* (2025.01); *A61K 40/19* (2025.01); *A61K 40/31* (2025.01); *A61P 35/00* (2018.01); *C07K 14/7051* (2013.01); *C07K 16/28* (2013.01); *C07K 2317/569* (2013.01)

(58) Field of Classification Search
None
See application file for complete search history.

(56) References Cited

U.S. PATENT DOCUMENTS

| | | | | |
|---|---|---|---|---|
| 2018/0264047 A1* | 9/2018 | Hagihara | ............. | A61K 35/545 |
| 2023/0048051 A1* | 2/2023 | Johnson | .................... | A01P 7/04 |
| 2023/0233678 A1* | 7/2023 | Xu | .................... | C07K 14/4746 |
| | | | | 424/277.1 |

OTHER PUBLICATIONS

Kapingidza et al. 2020. Antigen-Antibody Complexes. Vertebrate and Invertebrate Respiratory Proteins, Lipoproteins and other Body Fluid, CH 19, pp. 465-484 (Year: 2020).*
Culang et al. The structural basis of antibody-antigen recognition. Front. In Immun. 2013. vol. 4, Article 302 (Year: 2013).*
Clark et al. Influence of canonical structure determining residues on antibody affinity and stability. Journal of Structural Biology 185 (2014) 223-227 (Year: 2014).*

(Continued)

*Primary Examiner* — Amy E Juedes
*Assistant Examiner* — Hilary Ann Petrash

(57) ABSTRACT

The present application belongs to the technical field of biomedicine, and discloses a chimeric antigen receptor (CAR), an engineered dendritic cell (DC), and a use thereof. The CAR of the present application includes an extracellular domain, a CD8a hinge domain, a CD8a transmembrane domain, and an intracellular domain. The extracellular domain includes a guide sequence and a single-chain antibody sequentially. The intracellular domain includes a Dectin-1 intracellular domain and an intracellular domain of FcR gamma. Chimeric antigen receptor-modified dendritic cells (CAR-DCs) prepared with the CAR of the present application can efficiently recognize a tumor antigen. The combined administration of the CAR-DC and radiotherapy for treating a solid tumor can effectively overcome the immunosuppression of the tumor microenvironment and improve the clinical treatment effect. Therefore, the present application provides an effective immunotherapy strategy for clinical tumor patients, and provides a new idea and method for tumor immunotherapy.

13 Claims, 19 Drawing Sheets

Specification includes a Sequence Listing.

(56)          References Cited

OTHER PUBLICATIONS

Brown et al. Tolerance to Single, but Not Multiple, Amino Acid Replacements in Antibody VH, CDR2. J Immunol (1996) 156 (9):3285-3291 (Year: 1996).*

Tennenbaum et al. Radiotherapy potentiates the therapeutic efficacy of intratumoral dendritic cell administration. Cancer Research (2003), 63, 8466-8475 (Year: 2003).*

Lee et al. Medical X-band linear accelerator for high-precision radiotherapy. Medical Physics 2021, 48:5327-5342 (Year: 2021).*

* cited by examiner

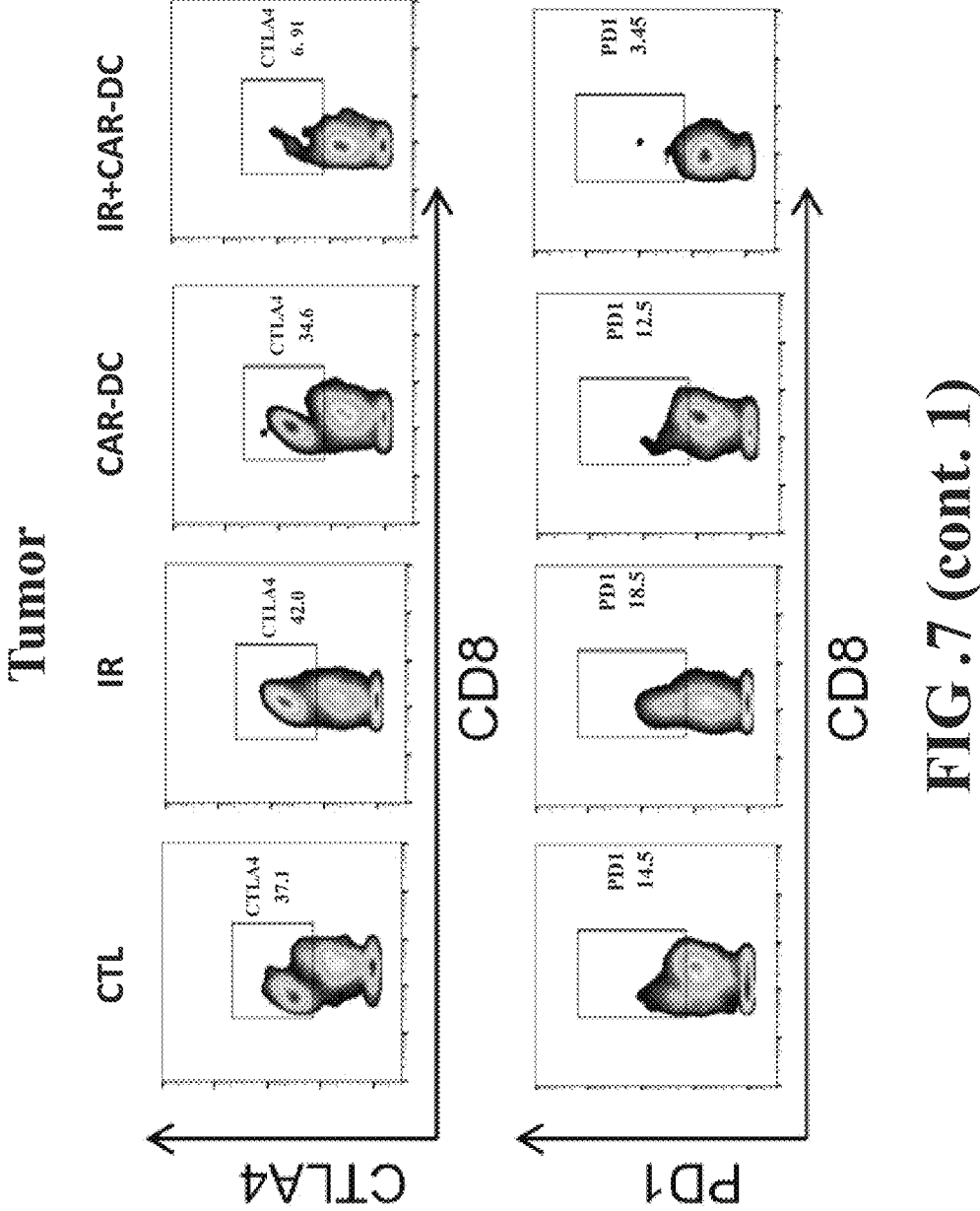
FIG .7 (cont. 1)

SEQUENCE LISTING

```
Sequence total quantity: 21
SEQ ID NO: 1              moltype = AA   length = 428
FEATURE                  Location/Qualifiers
source                   1..428
                         mol_type = protein
                         organism = synthetic construct
SEQUENCE: 1
MASPLTRFLS LNLLLLGESI ILGSGEADIQ MTQSPSSLSA SVGDRVTITC RASQYYSYYG   60
VAWYQQKPGK APKLLIYGAS YLYSGVPSRF SGSRSGTDFT LTISSLQPED FATYYCQQSF  120
YPITFGQGTK VEIKGGGGSG GGGSGGGGSE VQLVESGGGL VQPGGSLRLS CAASGFNLSG  180
GGVHWVRQAP GKGLEWVAGI YSSSGYTYYA DSVKGRFTIS ADTSKNTAYL QMNSLRAEDT  240
AVYYCARSSG GFDYWGQGTL VTVSSTTTKP VLRTPSPVHP TGTSQPQRPE DCRPRGSVKG  300
TGLDFACDIY IWAPLAGICV ALLLSLIITL ICYHRSRGVA IPRWPSSPAQ SGKESGRPRK  360
HIDQTSFDLQ TYGDEDLNEI HSHYKMRLKI QVRKAAIASR EKADAVYTGL NTRSQETYET  420
LKHEKPPQ                                                           428

SEQ ID NO: 2              moltype = DNA   length = 1287
FEATURE                  Location/Qualifiers
source                   1..1287
                         mol_type = other DNA
                         organism = synthetic construct
SEQUENCE: 2
atggccagcc ctctgaccag attcctgtct ctgaacctgc tcctgctggg agagtctatc   60
atcctgggat caggagaggc tgacatccag atgacccaga gcccttcctc actgagcgct  120
tccgtgggtg acagagtgac tattacctgc agagccagcc agtactacag ctactatgga  180
gtggcctggt accagcagaa gcctggcaaa gctcctaagc tgctgatcta tggagcttct  240
tacctgtact ccggggtccc atctaggttc agcggctcta ggtctggcac cgacttcact  300
ctgaccatct ccagcctgca gccagaagac ttcgccacct actactgcca gcagagtttc  360
tacccatca ccttcggaca gggaaccaag gtggaaatca aaggcggcgg cgggagcggg  420
ggcggcggct ctggaggcgg cgggtccgaa gtccagctgg tggagagcgg cggaggtctg  480
gtgcagccag gcggctccct gagactgtcc tgcgccgcct ccggcttcaa cctgtccggg  540
ggtggagtgc actgggtgag gcaggctccc ggcaagggac tggagtgggt ggctggaatc  600
tactccagct ccggatacac atactatgcc gacagcgtga agggcaggtt taccatcagc  660
gccgacacct ctaaaaacac cgcatacctg cagatgaata gcctgcgagc cgaggataca  720
gccgtgtatt actgcgccag gagctccggc ggctttgatt actgggggca gggcactctg  780
gtgactgtgt cctctacaac aactaagcct gtgctgagga cccccttccc tgtgcaccca  840
accggcacca gccagcccca gcgacctgag gactgcgaca cccgggggatc tgtgaagggc  900
accgggctgg attttgcatg tgacatttat atctgggccc ctctggccag catctgcgtg  960
gccctgctgc tgtctctgat cattaccctg atctgctatc atagatccag aggggtggct 1020
atccccagat ggcctagcag cccagcccag agtggaaaag agagcggccg ccctagaaag 1080
cacatcgacc agacctcttt tgatctgcaa acttacggtg acgaggatct gaatgagatc 1140
cactctcact acaagatgag gctgaagata caggtgcgga aggcagccat cgcaagcaga 1200
gagaaggccg acgccgtgta cacaggcctg aacacaagat ctcaggagac ctatgagacc 1260
ctgaagcatg agaagccccc ccagtga                                     1287

SEQ ID NO: 3              moltype = AA   length = 27
FEATURE                  Location/Qualifiers
source                   1..27
                         mol_type = protein
                         organism = Mus musculus
SEQUENCE: 3
MASPLTRFLS LNLLLLGESI ILGSGEA                                       27
```

-continued

```
SEQ ID NO: 4               moltype = DNA   length = 81
FEATURE                    Location/Qualifiers
source                     1..81
                           mol_type = genomic DNA
                           organism = Mus musculus
SEQUENCE: 4
atggccagcc ctctgaccag attcctgtct ctgaacctgc tcctgctggg agagtctatc   60
atcctgggat caggagaggc t                                             81

SEQ ID NO: 5               moltype = AA   length = 107
FEATURE                    Location/Qualifiers
source                     1..107
                           mol_type = protein
                           organism = synthetic construct
SEQUENCE: 5
DIQMTQSPSS LSASVGDRVT ITCRASQYYS YYGVAWYQQK PGKAPKLLIY GASYLYSGVP   60
SRFSGSRSGT DFTLTISSLQ PEDFATYYCQ QSFYPITFGQ GTKVEIK                107

SEQ ID NO: 6               moltype = DNA   length = 321
FEATURE                    Location/Qualifiers
source                     1..321
                           mol_type = other DNA
                           organism = synthetic construct
SEQUENCE: 6
gacatccaga tgacccagag cccttcctca ctgagcgctt ccgtgggtga cagagtgact   60
attacctgca gagccagcca gtactacagc tactatggag tggcctggta ccagcagaag   120
cctggcaaag ctcctaagct gctgatctat ggagcttctt acctgtactc cggggtccca   180
tctaggttca gcggctctag gtctggcacc gacttcactc tgaccatctc cagcctgcag   240
ccagaagact tcgccaccta ctactgccag cagagtttct accccatcac cttcggacag   300
ggaaccaagg tggaaatcaa a                                             321

SEQ ID NO: 7               moltype = AA   length = 116
FEATURE                    Location/Qualifiers
source                     1..116
                           mol_type = protein
                           organism = synthetic construct
SEQUENCE: 7
EVQLVESGGG LVQPGGSLRL SCAASGFNLS GGGVHWVRQA PGKGLEWVAG IYSSSGYTYY   60
ADSVKGRFTI SADTSKNTAY LQMNSLRAED TAVYYCARSS GGFDYWGQGT LVTVSS      116

SEQ ID NO: 8               moltype = DNA   length = 348
FEATURE                    Location/Qualifiers
source                     1..348
                           mol_type = other DNA
                           organism = synthetic construct
SEQUENCE: 8
gaagtccagc tggtggagag cggcggaggt ctggtgcagc caggcggctc cctgagactg   60
tcctgcgccg cctccggctt caacctgtcc gggggtggag tgcactgggt gaggcaggct   120
cccggcaagg gactggagtg ggtggctgga atctactcca gctccggata cacatactat   180
gccgacagcg tgaagggcag gtttaccatc agcgccgaca cctctaaaaa caccgcatac   240
ctgcagatga atagcctgcg agccgaggat acagccgtgt attactgcgc caggagctcc   300
ggcggctttg attactgggg gcagggcact ctggtgactg tgtcctct              348

SEQ ID NO: 9               moltype = AA   length = 15
FEATURE                    Location/Qualifiers
source                     1..15
                           mol_type = protein
                           organism = synthetic construct
SEQUENCE: 9
GGGGSGGGGS GGGGS                                                    15

SEQ ID NO: 10              moltype = DNA   length = 45
FEATURE                    Location/Qualifiers
source                     1..45
                           mol_type = other DNA
                           organism = synthetic construct
SEQUENCE: 10
ggcggcggcg ggagcggggg cggcggctct ggaggcggcg ggtcc                  45

SEQ ID NO: 11              moltype = AA   length = 45
FEATURE                    Location/Qualifiers
source                     1..45
                           mol_type = protein
                           organism = synthetic construct
SEQUENCE: 11
TTTKPVLRTP SPVHPTGTSQ PQRPEDCRPR GSVKGTGLDF ACDIY                  45

SEQ ID NO: 12              moltype = DNA   length = 135
```

```
FEATURE                 Location/Qualifiers
source                  1..135
                        mol_type = other DNA
                        organism = synthetic construct
SEQUENCE: 12
acaacaacta agcctgtgct gaggacccct tcccctgtgc acccaaccgg caccagccag    60
ccccagcgac ctgaggactg cagacccccgg ggatctgtga agggcaccgg gctggatttt  120
gcatgtgaca tttat                                                    135

SEQ ID NO: 13           moltype = AA  length = 27
FEATURE                 Location/Qualifiers
source                  1..27
                        mol_type = protein
                        organism = Mus musculus
SEQUENCE: 13
IWAPLAGICV ALLLSLIITL ICYHRSR                                         27

SEQ ID NO: 14           moltype = DNA  length = 81
FEATURE                 Location/Qualifiers
source                  1..81
                        mol_type = other DNA
                        organism = synthetic construct
SEQUENCE: 14
atctgggccc ctctggccgg catctgcgtg gccctgctgc tgtctctgat cattaccctg    60
atctgctatc atagatccag a                                              81

SEQ ID NO: 15           moltype = AA  length = 49
FEATURE                 Location/Qualifiers
source                  1..49
                        mol_type = protein
                        organism = synthetic construct
SEQUENCE: 15
GVAIPRWPSS PAQSGKESGR PRKHIDQTSF DLQTYGDEDL NEIHSHYKM                 49

SEQ ID NO: 16           moltype = DNA  length = 147
FEATURE                 Location/Qualifiers
source                  1..147
                        mol_type = other DNA
                        organism = synthetic construct
SEQUENCE: 16
ggggtggcta tccccagatg gcctagcagc ccagcccaga gtggaaaaga gagcggccgc    60
cctagaaagc acatcgacca gacctctttt gatctgcaaa cttacggtga cgaggatctg   120
aatgagatcc actctcacta caagatg                                       147

SEQ ID NO: 17           moltype = AA  length = 42
FEATURE                 Location/Qualifiers
source                  1..42
                        mol_type = protein
                        organism = Mus musculus
SEQUENCE: 17
RLKIQVRKAA IASREKADAV YTGLNTRSQE TYETLKHEKP PQ                        42

SEQ ID NO: 18           moltype = DNA  length = 126
FEATURE                 Location/Qualifiers
source                  1..126
                        mol_type = other DNA
                        organism = synthetic construct
SEQUENCE: 18
aggctgaaga tacaggtgcg gaaggcagcc atcgcaagca gagagaaggc cgacgccgtg    60
tacacaggcc tgaacacaag atctcaggag acctatgaga ccctgaagca tgagaagccc   120
ccccag                                                              126

SEQ ID NO: 19           moltype = DNA  length = 50
FEATURE                 Location/Qualifiers
source                  1..50
                        mol_type = other DNA
                        organism = synthetic construct
SEQUENCE: 19
ataatacgac tcactatagg gagagccacc atggccagcc tctctgaccag               50

SEQ ID NO: 20           moltype = DNA  length = 50
FEATURE                 Location/Qualifiers
source                  1..50
                        mol_type = other DNA
                        organism = synthetic construct
SEQUENCE: 20
ttttttttttt tttctgtctt tttattgccg tcactggggg ggcttctcat               50

SEQ ID NO: 21           moltype = AA  length = 413
```

-continued

```
FEATURE              Location/Qualifiers
source               1..413
                     mol_type = protein
                     organism = synthetic construct
SEQUENCE: 21
MALPVTALLL PLALLLHAAR PQVQLLESGG GLVQPGGSLR LSCAASGFTF SSYTMSWVRQ  60
APGQALEWMG TISSRGTYTY YPDSVKGRFT ISRDNAKNSL YLQMNSLRAE DTAVYYCARE  120
AIFTHWGRGT LVTVSSGGGG SGGGGSGGGG SDIQLTQSPS SLSASVGDRV TITCKASQDI  180
NNYHSWYQQK PGQAPRLLIY RANRLVDGVP DRFSGSGYGT DFTLTINNIE SEDAAYYFCL  240
KYNVFPYTFG QGTKVEIKTT TPAPRPPTPA PTIASQPLSL RPEACRPAAG GAVHTRGLDF  300
ACDIYIWAPL AGTCGVLLLS LVITLYCRWP PSAACSGKES VVAIRTNSQS DFHLQTYGDE  360
DLNELDPHYE MRLKIQVRKA AITSYEKSDG VYTGLSTRNQ ETYETLKHEK PPQ         413
```

ENGINEERED DENDRITIC CELL AND USE THEREOF

TECHNICAL FIELD

The present application relates to the technical field of biomedicine, and specifically to an engineered dendritic cell (DC) and a use thereof.

REFERENCE TO SEQUENCE LISTING

The Sequence Listing XML file submitted via the USPTO Patent Center, with a file name of "Sequence listing_SCH-25009-USPT.xml", a creation date of Jan. 18, 2025, and a size of 22,777 bytes, is part of the specification and is incorporated in its entirety by reference herein.

BACKGROUND

Dendritic cells (DCs), as important immune cells, play a key role in the activation of T cells and the enhancement of anti-tumor immune responses. In the tumor therapy research, DCs are often used in the form of DC-based tumor vaccines for the prevention and treatment of tumors. In 2010, the first therapeutic cancer vaccine worldwide, Provenge (Sipuleucel-T), was approved for the treatment of prostate cancer, marking the important development of therapeutic cancer vaccines. However, despite the early success of Provenge and the generally accepted safety of the conventional DC-based cancer vaccines, these cancer vaccines often exhibit undesired clinical manifestations, and only 5% to 15% of patients acquire an objective immune response. The limited efficacy of cancer vaccines may be mainly attributed to the presence of various immunosuppressive factors in the tumor microenvironment. These immunosuppressive factors act as immunomodulators to inhibit the responses of anti-tumor T cells, thereby inhibiting the clinical effects of cancer vaccines as a whole.

Therefore, the new generation of DC vaccines must overcome multiple immunosuppressive mechanisms in the tumor microenvironment to improve the anti-tumor response mediated by effector T cells. How to improve the activity and anti-tumor effect of DCs in the tumor microenvironment is one of the major challenges for the current research.

SUMMARY

An objective of the present application is to overcome the deficiencies of the prior art and provide an engineered DC and a use thereof.

In order to achieve the above objective, the present application adopts the following technical solutions:

In a first aspect, the present application provides a chimeric antigen receptor (CAR), including an extracellular domain, a CD8a hinge domain, a CD8a transmembrane domain, and an intracellular domain.

The extracellular domain includes a guide sequence and a single-chain antibody sequentially (for example, from N-terminus to C-terminus).

The guide sequence has an amino acid sequence set forth in SEQ ID NO: 3, or has an amino acid sequence that has a homology of 98% or more and preferably 99% or more with the amino acid sequence set forth in SEQ ID NO: 3.

The single-chain antibody includes amino acid sequences set forth in SEQ ID NOs: 5, 7, and 9 sequentially (for example, from N-terminus to C-terminus), or includes amino acid sequences having a homology of 98% or more and preferably 99% or more with the amino acid sequences set forth in SEQ ID NOs: 5, 7, and 9 sequentially.

The intracellular domain includes a Dectin-1 intracellular domain and an intracellular domain of FcR gamma.

In the present application, a CAR is designed by a genetic engineering technology and used for modifying DCs to enhance a function of the DCs. The prepared CAR-DCs can efficiently recognize tumor antigens, transmit an extracellular signal inside cells, activate an intracellular signaling pathway, and further activate DCs. Moreover, the CAR-DCs can reverse the tumor microenvironment and improve the immune response, and can induce a specific immune response in vivo by acquiring a tumor antigen and presenting the tumor antigen to T cells. The radiotherapy can enhance an immune response in the body, and provides a basis for the activation and function improvement of DCs by directly killing tumor cells and releasing antigens. The combined use of the radiotherapy with the CAR-DC of the present application can improve an activation effect for DCs, increase the infiltration of immune cells through the local inflammation caused by the radiotherapy, and improve the efficacy of the radiotherapy by enhancing an anti-tumor immune effect of DCs, thereby improving the overall anti-tumor effect.

As a preferred embodiment of the CAR of the present application, the CD8a hinge domain has an amino acid sequence set forth in SEQ ID NO: 11, or has an amino acid sequence that has a homology of 98% or more and preferably 99% or more with the amino acid sequence set forth in SEQ ID NO: 11; and the CD8a transmembrane domain has an amino acid sequence set forth in SEQ ID NO: 13, or has an amino acid sequence that has a homology of 98% or more and preferably 99% or more with the amino acid sequence set forth in SEQ ID NO: 13.

As a preferred embodiment of the CAR of the present application, the Dectin-1 intracellular domain has an amino acid sequence set forth in SEQ ID NO: 15, or has an amino acid sequence that has a homology of 98% or more and preferably 99% or more with the amino acid sequence set forth in SEQ ID NO: 15; and the intracellular domain of FcR gamma has an amino acid sequence set forth in SEQ ID NO: 17, or has an amino acid sequence that has a homology of 98% or more and preferably 99% or more with the amino acid sequence set forth in SEQ ID NO: 17.

As a preferred embodiment of the CAR of the present application, the CAR has an amino acid sequence set forth in SEQ ID NO: 1, or has an amino acid sequence that has a homology of 98% or more and preferably 99% or more with the amino acid sequence set forth in SEQ ID NO: 1.

In a second aspect, the present application provides a nucleic acid encoding the CAR, where the nucleic acid has a nucleotide sequence set forth in SEQ ID NO: 2, or has a nucleotide sequence that has a homology of 98% or more and preferably 99% or more with the nucleotide sequence set forth in SEQ ID NO: 2.

In a third aspect, the present application provides an engineered DC (CAR-DC) modified with the CAR.

In a fourth aspect, the present application provides an engineered DC (CAR-DC) including a nucleic acid encoding the CAR.

As a preferred embodiment of the engineered DC of the present application, the engineered DC is at least one selected from the group consisting of a peripheral blood mononuclear cell, a hematopoietic stem cell, an induced pluripotent stem cell, and an embryonic stem cell.

In a fifth aspect, the present application provides a preparation method of an engineered DC, including the following step: transforming DNA or mRNA encoding the CAR into a DC, and allowing an expression.

As a preferred embodiment of the preparation method of an engineered DC of the present application, a vector tool for the transforming includes any one selected from the group consisting of an expression plasmid, a lentivirus, and a liposome.

In a sixth aspect, the present application provides a use of a CAR and an engineered DC in preparation of a tumor radiosensitizer administered in combination with radiotherapy, where the CAR is the CAR described above or a CAR having an amino acid sequence set forth in SEQ ID NO: 21; and the engineered DC is the engineered DC described above, or a DC modified with a CAR having an amino acid sequence set forth in SEQ ID NO: 21.

Correspondingly, the present application also provides a preparation for tumor radiosensitization administered in combination with radiotherapy, including a CAR and an engineered DC, where the CAR is the CAR described above or a CAR having an amino acid sequence set forth in SEQ ID NO: 21; and the engineered DC is the engineered DC described above, or a DC modified with a CAR having an amino acid sequence set forth in SEQ ID NO: 21.

In a seventh aspect, the present application provides a drug or preparation for treating a tumor, including the engineered DC, a pharmaceutically acceptable adjuvant, and/or a carrier or an excipient acceptable in a preparation process.

In an eighth aspect, the present application provides a method for treating a tumor, including: administering at least one of the following cells or drug to a tumor patient in combination with radiotherapy:

i, the engineered DC described above;

ii, the tumor therapeutic drug described above; and iii, a DC modified with a CAR having an amino acid sequence set forth in SEQ ID NO: 21.

As a preferred embodiment of the method for treating a tumor of the present application, the radiotherapy includes external beam radiation therapy and/or intracavitary radiotherapy.

As a further preferred embodiment of the method for treating a tumor of the present application, the external beam radiation therapy includes at least one selected from the group consisting of an X-knife, a gamma knife, and a linear accelerator; and the intracavitary radiotherapy includes seed implantation.

As a preferred embodiment of the method for treating a tumor of the present application, the tumor includes any one selected from the group consisting of breast cancer, lung cancer, colorectal cancer, liver cancer, pancreatic cancer, melanoma, glioma, ovarian cancer, and prostate cancer.

As a preferred embodiment of the method for treating a tumor of the present application, a process of the administering includes: on day 1 of the treating, intravenously injecting the engineered DC or the tumor therapeutic drug; on day 2 of the treating, applying the radiotherapy; and on day 7 of the treating, intravenously injecting the engineered DC or the tumor therapeutic drug into the tumor patient.

Compared with the prior art, the present application has the following beneficial effects:

In the present application, CAR-DC is used in combination with radiotherapy (including local radiotherapy and systemic radiotherapy) to treat solid tumors (including solid tumors that are sensitive or insensitive to the radiotherapy). The CAR-DC can enhance the immune effect of the radiotherapy in the tumor microenvironment, effectively overcome the immunosuppression of the tumor microenvironment, and improve the clinical treatment effect. Therefore, the present application provides an effective immunotherapy strategy for clinical tumor patients, and provides a new idea and method for tumor immunotherapy.

DETAILED DESCRIPTION

To well explain the objective, technical solutions, and advantages of the present application, the present application will be further explained below with reference to specific examples. It should be understood by those skilled in the art that the specific examples described here are merely intended to explain the present application, rather than to limit the present application.

In the examples, unless otherwise specified, the experimental methods used are conventional, and the materials and reagents used are commercially available.

In the following examples, a method of plotting a tumor growth curve is as follows: A tumor is periodically measured for a length and a width by an electronic vernier caliper. A volume of the tumor is calculated based on the length and the width of the tumor according to the following calculation formula: (width^2*length)/2. The tumor growth curve is plotted with the Prism Graphad software.

Example 1: Engineered DC (CAR-DC)

1. Design of an Engineered DC (CAR-DC)

Figure 1:
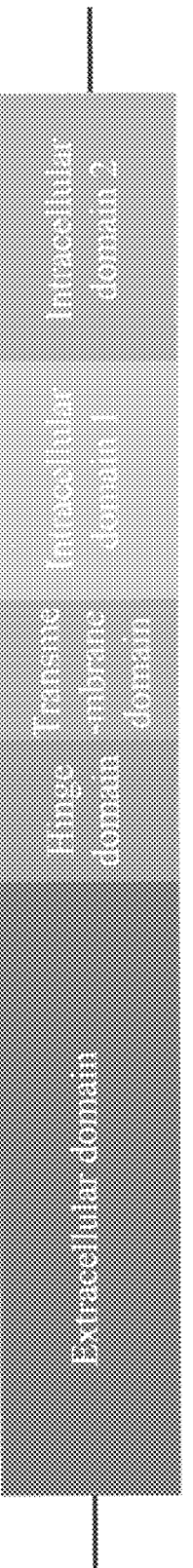
FIG. 1 is a schematic diagram of the structure of CAR-DC.

Functional elements of CAR are shown in FIG. 1. The structure of the CAR includes an extracellular domain, a hinge domain, a transmembrane domain, and an intracellular domain (an amino acid sequence of mouse Epha2 CAR is set forth in SEQ ID NO: 1).

The extracellular domain includes a guide sequence (the amino acid sequence of a mouse Epha2 CAR guide sequence is set forth in SEQ ID NO: 3), a single-chain antibody (scFv) (the amino acid sequence of anti-mouse Epha2 VH is set forth in SEQ ID NO: 5, the amino acid sequence of anti-mouse Epha2 VL is set forth in SEQ ID NO: 7, and the amino acid sequence for a mouse Epha2 CAR linker is set forth in SEQ ID NO: 9). The hinge domain (the amino acid sequence of a mouse CD8 hinge domain is set forth in SEQ ID NO: 11) and the transmembrane domain (the amino acid sequence of a mouse CD8a transmembrane domain is set forth in SEQ ID NO: 13) are a hinge domain and a transmembrane domain of CD8a, respectively. The intracellular domain employs human or mouse Dectin-1 (the amino acid sequence of a mouse Dectin1 intracellular domain is set forth in SEQ ID NO: 15) and an intracellular domain of FcR gamma (the amino acid sequence of an intracellular domain of mouse FcR gamma is set forth in SEQ ID NO: 17). After being combined, the amino acid sequences of the elements were optimized by a codon optimization technology. A DNA sequence for mouse CAR-DC was cloned into a pCDH-CMV-MCS-EF1-copGFP-T2A-Puro vector.

2. In Vitro Transcription

A gene for the CAR-DC was amplified by PCR. A PCR system (100 μL system) was as follows: DNA (amplified with a codon-optimized base sequence set forth in SEQ ID NO: 2 as a template): 100 ng, 2×Taq mix: 50 μL, primer mix (5 μM): 5 μL, and H₂O: to 100 μL. Primer sequences were set forth in SEQ ID NOs: 19 and 20, respectively. Amplification conditions were as follows: 1. 94° C.: 5 min; 2. 94° C.: 20 s, 55° C.: 30 s, and 72° C.: 60 s, with 30 cycles; 3. 72° C.: 5 min; and 4. 4° C.: heat preservation.

CAR-DC mRNA carrying a T7 promoter and a PolyA structure was produced through the transcription with a High Yield T7 RNA Synthesis Kit (HONGENE BIOTECH, Shanghai). A transcription system was as follows: template DNA (4 μg), ATP (8 μL), GTP (8 μL), CTP (8 μL), UTP (8 μL), GAG (8 μL), Reaction buffer (20 μL), Enzyme (7.5 μL), ultrapure water (to 100 μL). The transcription system was incubated at 37° C. for 4 h, then 7.5 μL of DNase was added, and a resulting mixture was incubated at 37° C. for 15 min. After a reaction was completed, mRNA was precipitated with lithium chloride. 150 μL of ultrapure water and 150 μL of a lithium chloride solution were added to a reaction system to precipitate RNA. A resulting mixed system was thoroughly mixed, refrigerated at −20° C. for 60 min, and centrifuged at 4° C. and a maximum rotational speed for 5 min to produce a supernatant and a precipitate. The supernatant was carefully removed. The precipitate was washed with 1 mL of about 70% ethanol, and then the 70% ethanol was carefully removed to produce a washed precipitate. The washed precipitate was air-dried and then resuspended with an appropriate amount of nuclease-free water.

3. Preparation of CAR-DCs

Tibias and fibulas of hind legs of 6-8 week-old C57BL6 or Balbc mice were collected. The bone marrow was flushed out by a 1 ml syringe, properly ground into a single-cell suspension, and centrifuged at 1,500 rpm for 5 min, and a resulting supernatant was removed. Red blood cells were lysed with a 1×ACK buffer. Centrifugation was conducted at 1,500 rpm for 5 min, and a resulting supernatant was removed. Cells were washed twice with phosphate buffered saline (PBS), counted, and inoculated in a 6-well plate at a density of 1×10⁶/mL. 100 ng/ml of GMCSF and IL4 were added to allow the differentiation of DCs. A medium was supplemented every 2 d to 3 d. After 8 d of differentiation, mouse DCs were harvested, counted, and electrotransformed with the above mRNA by a LONZA 4D system under the following conditions: 1E6-3E6/test, 100 μL P3 solution, 5 μg/test, and program CM150. The electrotransformed cells were inoculated in a 6-well plate and cultured for 24 h. Then an expression efficiency of CAR was measured with protein L. Resulting cells were used for downstream applications.

Figure 2:
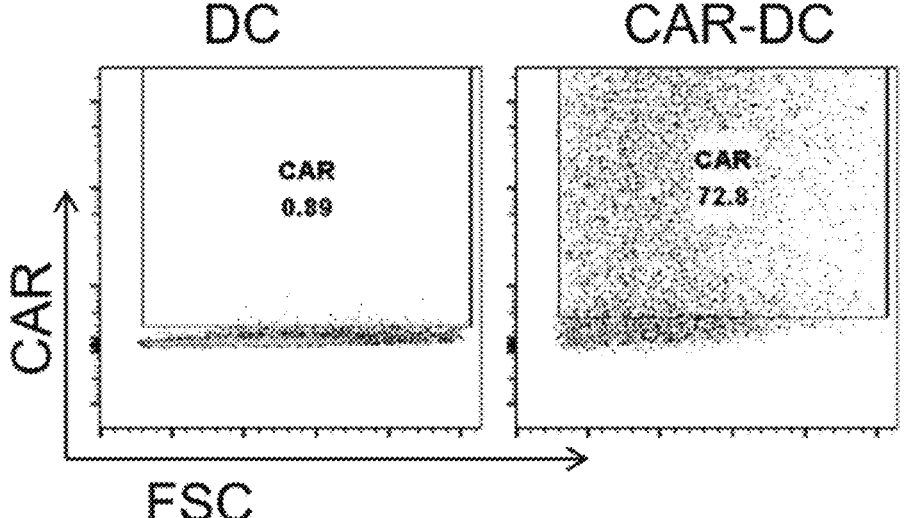
FIG. 2 shows the expression of CAR on a surface of mouse bone marrow-derived DCs that is detected by flow cytometry.

Example 2 Treatment of Colorectal Cancer with a Combination of CAR-DCs and Radiotherapy Tibias and fibulas of hind legs of 6-8 week-old C57BL6 mice were collected by the method in Example 1 to prepare CAR-DCs. An expression efficiency of CAR was detected with protein L. Results were shown in FIG. 2. A transfection efficiency of CAR in DCs was 72.8%.

Figure 3:
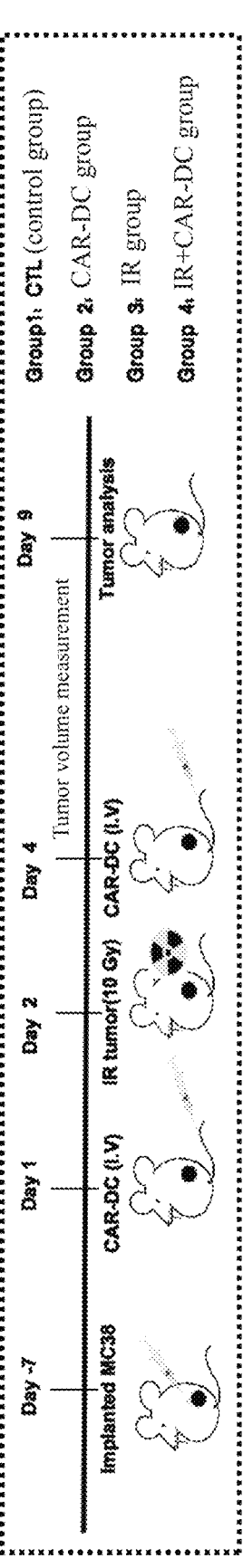
FIG. 3 is a flow chart of an animal experiment in which colorectal cancer MC38 in mice is treated with a combination of CAR-DC and radiotherapy.

Mouse colorectal cancer cells MC38 were transplanted into C57BL6 mice (6 weeks to 8 weeks). One week after the tumor transplantation, the mice were randomly divided into the following four groups: a control group (CTL), a CAR-DC group, a radiotherapy group (IR), and a radiotherapy+CAR-DC group (IR+CAR-DC). On day 1, mice in the CAR-DC group and the radiotherapy+CAR-DC group each were infused with CAR-DCs through the tail vein at a dose of 3×10⁶ cells/mouse. On day 2, mice in the radiotherapy group and the radiotherapy+CAR-DC group each were subjected to X-ray irradiation at an irradiation dose of 10 Gy. On day 4, CAR-DCs were infused through the tail vein for the second time at a dose of 3×10⁶ cells/mouse. The growth and survival of mouse tumors were continuously observed. A specific flow chart was shown in FIG. 3.

At the end of the experiment, the mouse tumors were collected for analysis. The tumors were grouped and arranged, photographed, and weighed by a balance. Data was collected. Tumor tissues were digested with a collagenase to produce single cells. The single cells were labeled with CD45 (BD Pharmingen™, 564279), CD3 (BD Pharmingen™, 560591), CD8 (BD Pharmingen™, 553031), CTLA4 (BD Pharmingen™, 553720), and PDI (BD Pharmingen™, 749422) antibodies, incubated for 30 min on ice in the dark, washed to remove non-specifically bound antibodies, resuspended with 400 μL of PBS, and analyzed by flow cytometry for a cell subtype and cell status.

Figure 4:
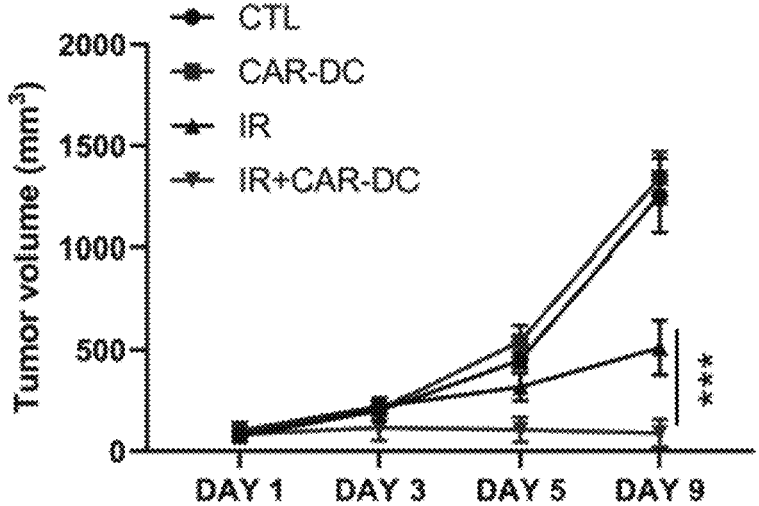
FIG. 4 shows tumor growth curves when colorectal cancer MC38 in mice is treated with a combination of CAR-DC and radiotherapy.
Figure 5:
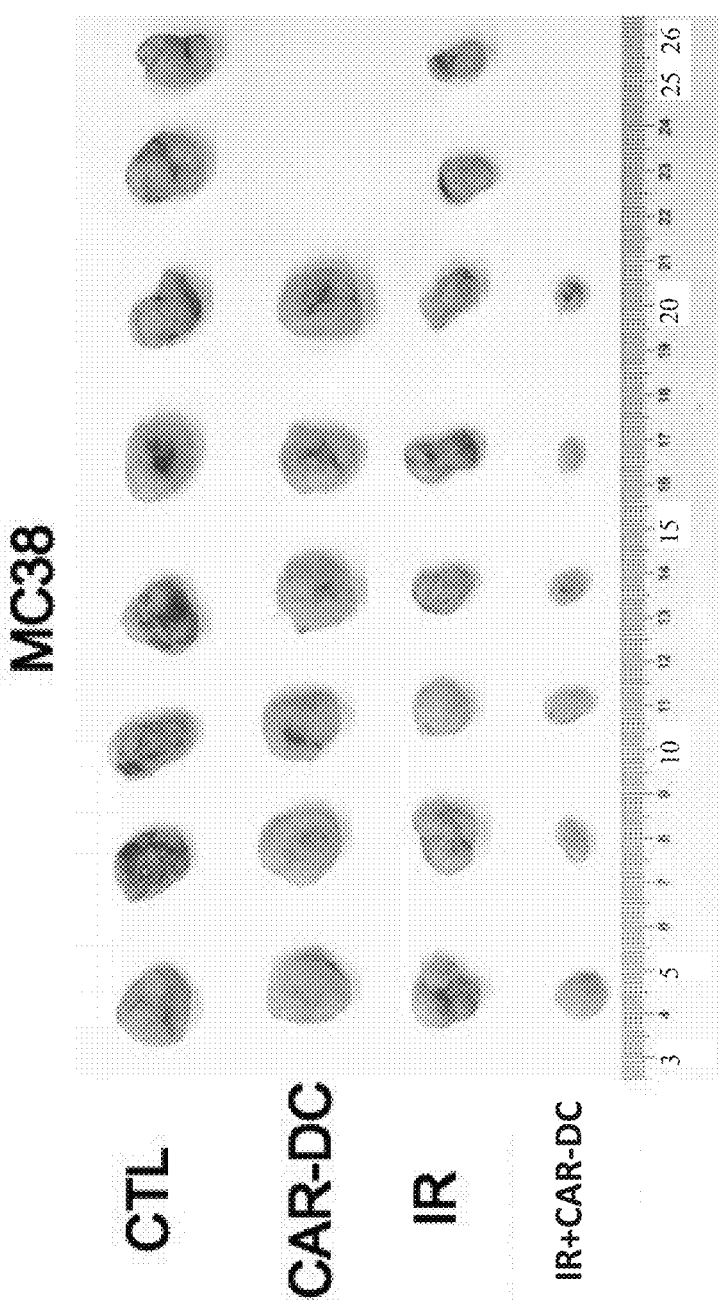
FIG. 5 shows pictures of tumors (Day 9) when colorectal cancer MC38 in mice is treated with a combination of CAR-DC and radiotherapy.
Figure 6:
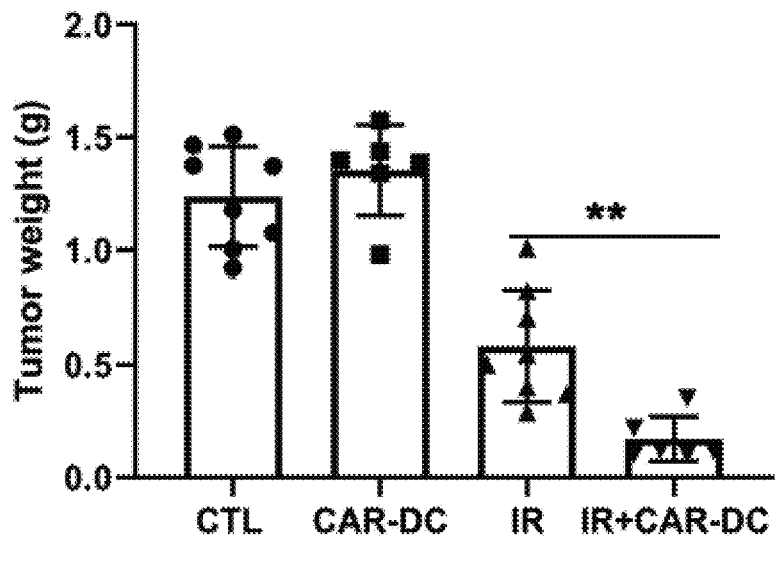
FIG. 6 shows tumor weights when colorectal cancer MC38 in mice is treated with a combination of CAR-DC and radiotherapy.
Figure 7:
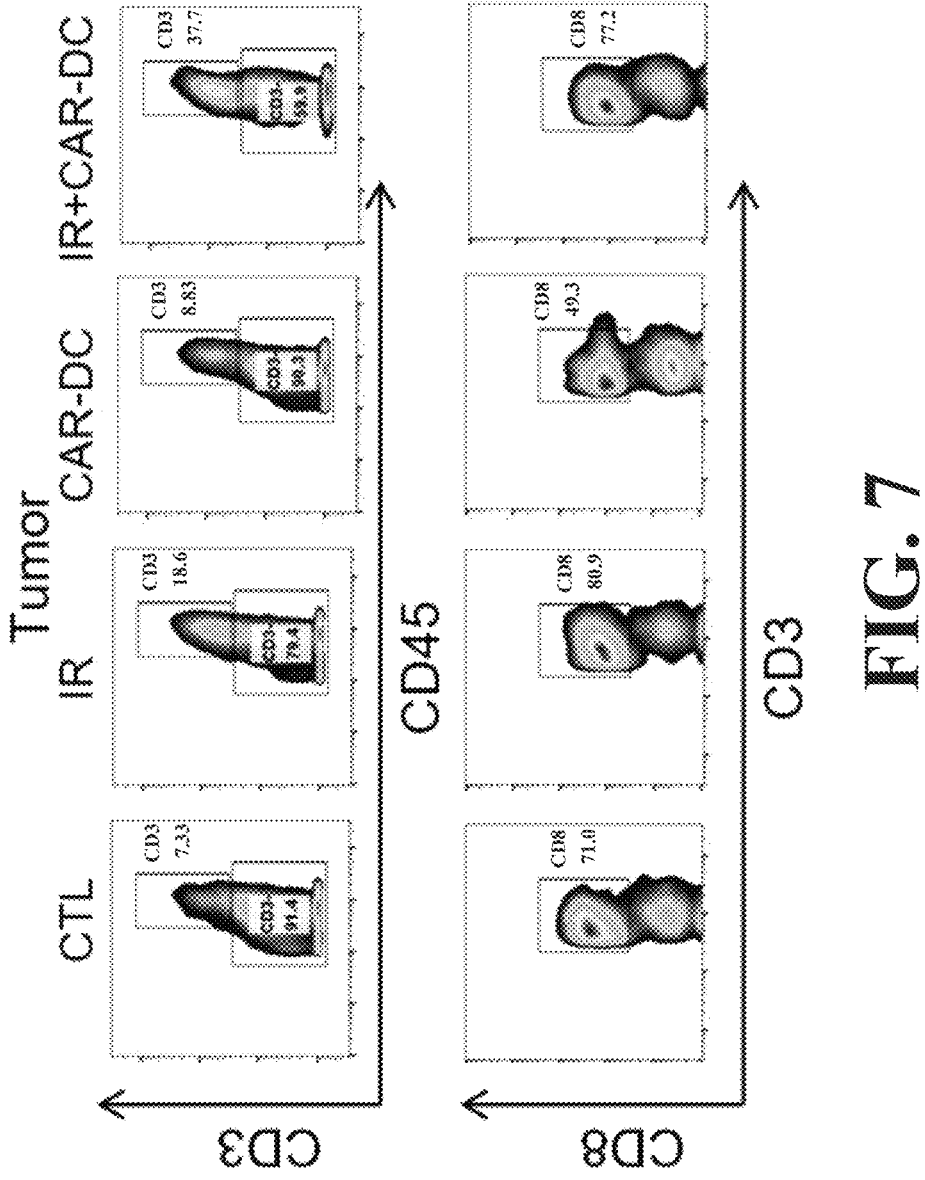
FIG. 7 shows flow cytometry results of tumor single cells when colorectal cancer MC38 in mice is treated with a combination of CAR-DC and radiotherapy.
Figure 8:
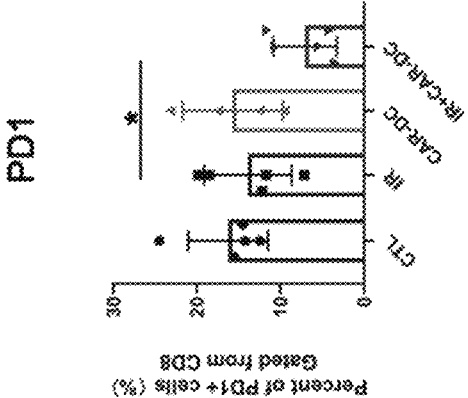
FIG. 8 shows statistical charts of flow cytometry results of tumor single cells when colorectal cancer MC38 in mice is treated with a combination of CAR-DC and radiotherapy.
Figure 8:
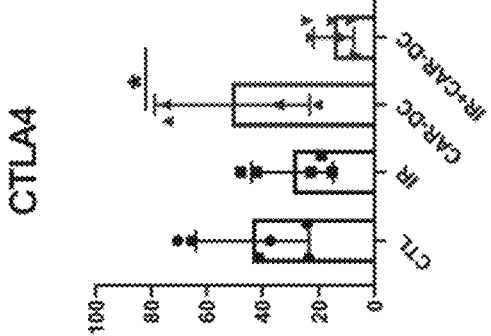
Figure 8:
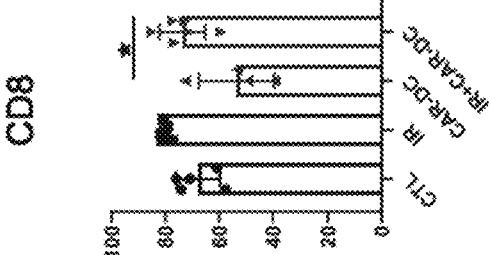
Figure 8:
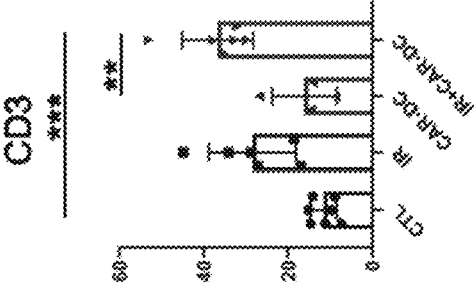

A therapeutic effect of the combination of the CAR-DC and the radiotherapy for tumors was evaluated. It could be seen from tumor growth curves (FIG. 4), tumor sizes (FIG. 5), and tumor weights (FIG. 6) that the combination of the CAR-DC and the radiotherapy had a significant inhibitory effect on the tumor growth (differences among groups were determined by t-test, $p<0.01$ and $*p<0.001$). In order to further analyze a phenotype of tumor-infiltrating T cells, single-cell suspensions were prepared from tumors, incubated with CD3, CD8, CTLA4, and PDI antibodies, and tested by flow cytometry for a cell subtype and phenotype (FIG. 7 and FIG. 8). Results showed that the combined use of the CAR-DC and the radiotherapy significantly increased the infiltration of T cells. In particular, the infiltration of effector T cells was significantly increased, and the infiltrating T cells exhibited lower exhausted phenotypes than T cells for animal tumors in other groups (differences among groups were determined by t-test, $*p<0.05$ and $**p<0.01$). It further explained a mechanism of the combination of the CAR-DC and the radiotherapy to achieve a prominent anti-tumor effect.

Figure 9:
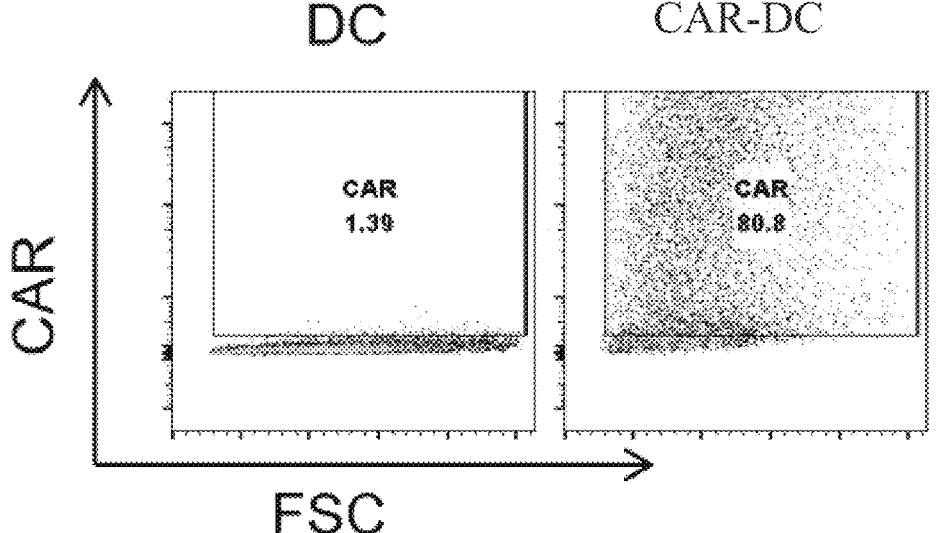
FIG. 9 shows the expression of CAR on a surface of mouse bone marrow-derived DCs that is detected by flow cytometry.

Example 3 Treatment of Lung Cancer with a Combination of CAR-DCs and Radiotherapy Tibias and fibulas of hind legs of 6-8 week-old Balbc mice were collected by the method in Example 1 to prepare CAR-DCs. An expression efficiency of CAR was detected with protein L. Results were shown in FIG. 9. A transfection efficiency of CAR in DCs was 80.8%.

Mouse lung cancer cells LLC were transplanted into C57BL6 mice (6 weeks to 8 weeks). 9 days after the tumor transplantation, the mice were randomly divided into the following four groups: a control group (CTL), a CAR-DC group, a radiotherapy group (IR), and a radiotherapy+CAR-DC group (IR+CAR-DC). On day 0, mice in the CAR-DC group and the radiotherapy+CAR-DC group each were infused with CAR-DCs through the tail vein at a dose of $3\times10^6$ cells/mouse. On day 1, mice in the radiotherapy group and the radiotherapy+CAR-DC group each were subjected to X-ray irradiation at an irradiation dose of 5 Gy. On day 3, CAR-DCs were infused through the tail vein for the second time at a dose of $3\times10^6$ cells/mouse. The growth and survival of mouse tumors were continuously observed.

At the end of the experiment, the mouse tumors were collected for analysis. The tumors were grouped and arranged, photographed, and weighed by a balance. Data was collected.

Figure 10:
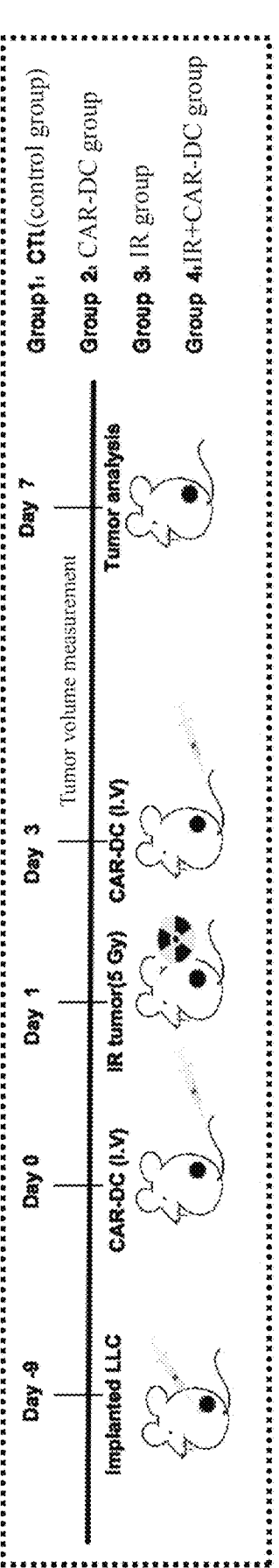
FIG. 10 is a flow chart of an animal experiment in which lung cancer LLC in mice is treated with a combination of CAR-DC and radiotherapy.
Figure 11:
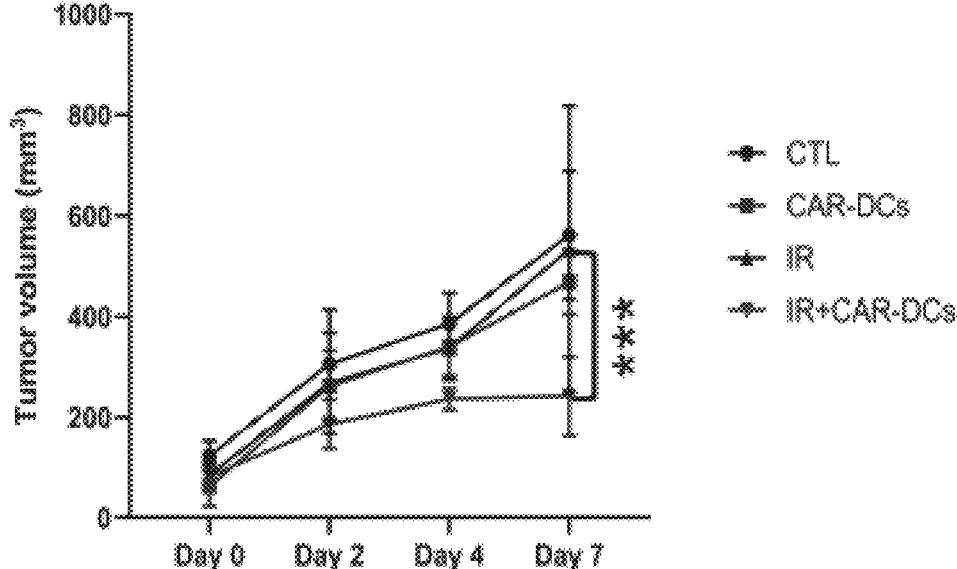
FIG. 11 shows tumor growth curves when lung cancer LLC in mice is treated with a combination of CAR-DC and radiotherapy.
Figure 12:
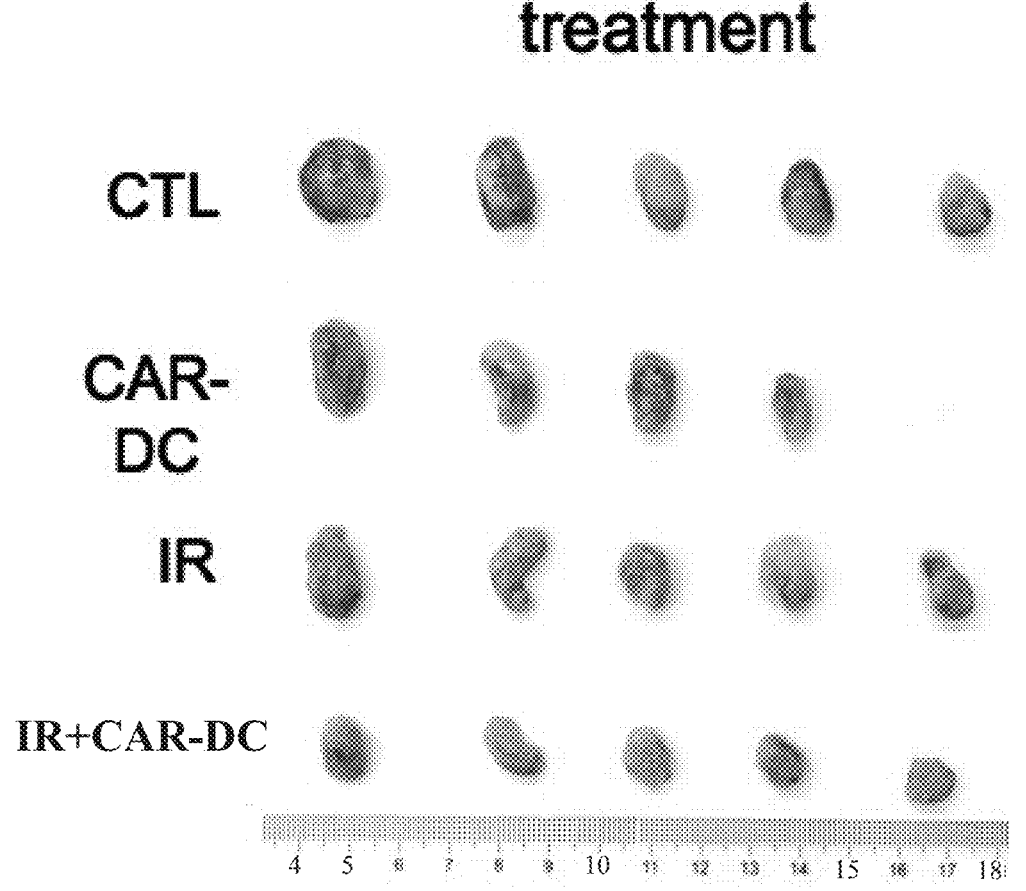
FIG. 12 shows pictures of tumors (Day 7) when lung cancer LLC in mice is treated with a combination of CAR-DC and radiotherapy.
Figure 13:
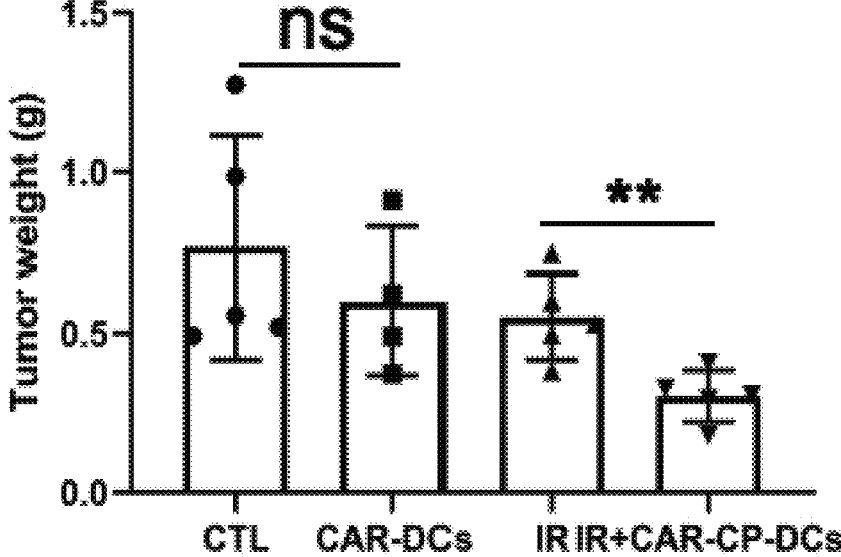
FIG. 13 shows tumor weights when lung cancer LLC8 in mice is treated with a combination of CAR-DC and radiotherapy.

The prepared CAR-DCs were administered in combination with the radiotherapy to LLC tumor-bearing mice (a flow chart was shown in FIG. 10) to evaluate a therapeutic effect of the combination of the CAR-DC and the radiotherapy for the tumor. It could be seen from tumor growth curves (FIG. 11), tumor sizes (FIG. 12), and tumor weights (FIG. 13) that the combination of the CAR-DC and the radiotherapy had a significant inhibitory effect on the growth of lung cancer (differences among groups were determined by t-test, $*p<0.05$ and $**p<0.01$).

Example 4 Treatment of Breast Cancer with a Combination of CAR-DCs and Radiotherapy Tibias of hind legs of 6-8 week-old Balbc mice were collected by the method in Example 1 to prepare CAR-DCs.

Figure 14:
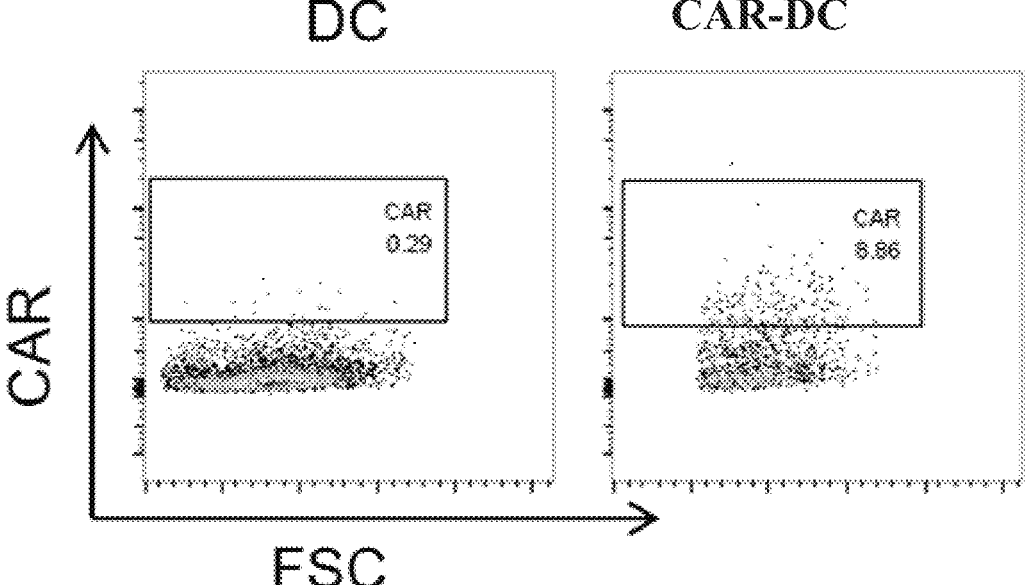
FIG. 14 shows the expression of CAR on a surface of mouse bone marrow-derived DCs that is detected by flow cytometry.

An expression efficiency of CAR was detected with protein L. Results were shown in FIG. 14. A transfection efficiency of CAR in DCs was 8.86%.

Mouse breast cancer cells 4T1 were transplanted into Balbc mice (6 weeks to 8 weeks). 9 days after the tumor transplantation, the mice were randomly divided into the following four groups: a control group (CTL), a CAR-DC group, a radiotherapy group (IR), and a radiotherapy+CAR-DC group (IR+CAR-DC). On day 0, mice in the CAR-DC group and the radiotherapy+CAR-DC group each were infused with CAR-DCs through the tail vein at a dose of $3\times10^6$ cells/mouse. On day 1, mice in the radiotherapy group and the radiotherapy+CAR-DC group each were subjected to X-ray irradiation at an irradiation dose of 5 Gy. On day 3, CAR-DCs were infused through the tail vein for the second time at a dose of $3\times10^6$ cells/mouse. The growth and survival of mouse tumors were continuously observed.

At the end of the experiment, the mouse tumors were collected for analysis. The tumors were grouped and arranged, photographed, and weighed by a balance. Data was collected.

Figure 15:
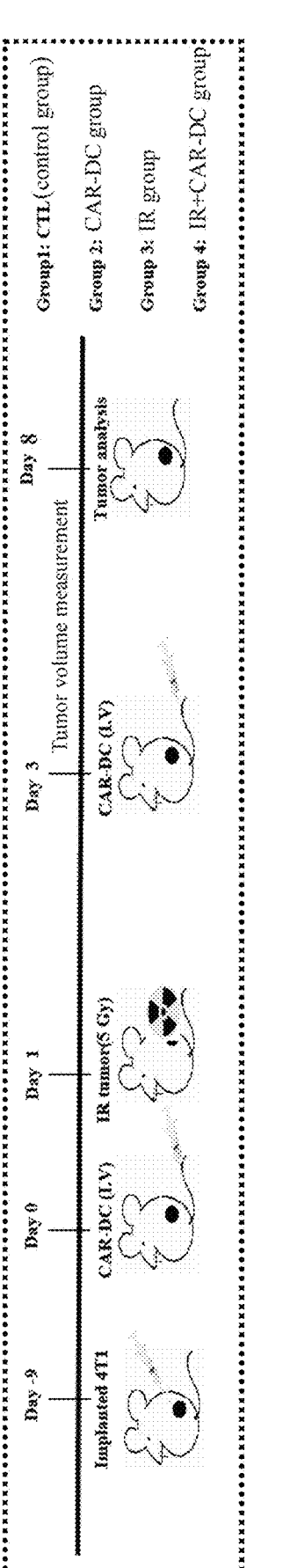
FIG. 15 is a flow chart of an animal experiment in which breast cancer 4T1 in mice is treated with a combination of CAR-DC and radiotherapy.
Figure 16:
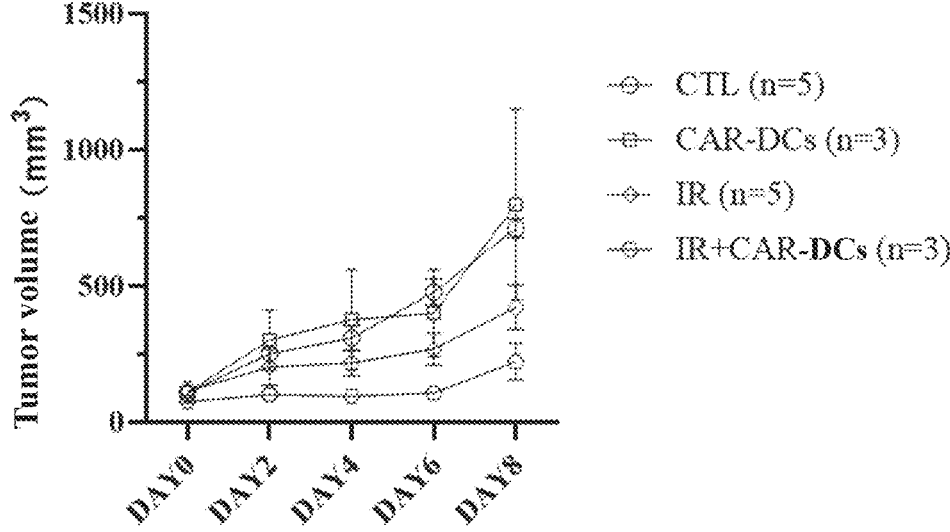
FIG. 16 shows tumor growth curves when breast cancer 4T1 in mice is treated with a combination of CAR-DC and radiotherapy.

The prepared CAR-DCs were administered in combination with the radiotherapy to LLC tumor-bearing mice (a flow chart was shown in FIG. 15) to evaluate a therapeutic effect of the combination of the CAR-DC and the radiotherapy for the tumor. It could be seen from tumor growth curves (FIG. 16) that the combination of the CAR-DC and the radiotherapy had a significant inhibitory effect on the growth of breast cancer.

Example 5 Treatment of Human Breast Cancer with a Combination of CAR-DCs and Radiotherapy Construction of humanized mice: Immunodeficient mice (purchased from Jiangsu GemPharmatech LLC., NCG, T001475) were irradiated at a sublethal dose. Then a human thymus tissue of about 1 $mm^3$ was transplanted into a renal capsule of each immunodeficient mouse, and a wound was sutured after the surgery. The mice each were injected with CD34+ hematopoietic stem cells through the tail vein after wake. 10 weeks after the surgery, blood was collected and tested to determine the reconstruction of an immune system in mice. 2 to 3 drops of intravenous blood were collected from a hind leg of each mouse, added to an EDTA-PBS buffer, and centrifuged to settle cells. Red blood cells were completely lysed with a 1×ACK lysis buffer until a transparent lysate solution was produced. The transparent lysate solution was centrifuged to produce a supernatant and a precipitate. The supernatant was removed. The precipitate was washed once with Dulbecco's phosphate-buffered saline (DPBS), then incubated with an anti-CAR antibody and an anti-CD11c antibody, then stained, washed once, resuspended in DPBS, and analyzed by flow cytometry to determine the successful reconstruction of humanized mice.

Preparation of humanized CAR-DCs: Tibias and fibulas of hind legs of the humanized mice were collected. The bone marrow was flushed out by a 1 ml syringe, properly ground into a single-cell suspension, and centrifuged at 1,500 rpm for 5 min, and a resulting supernatant was removed. Red blood cells were lysed with a 1×ACK buffer. Centrifugation was conducted at 1,500 rpm for 5 min, and a resulting supernatant was removed. Cells were washed twice with PBS, counted, and inoculated in a 6-well plate at a density of $1\times10^6$/mL. 100 ng/ml of human GMCSF and human IL4 were added to allow the differentiation of DCs. A medium was supplemented every 2 d to 3 d. After 8 d of differentiation, DCs were harvested, counted, and transfected with a

Figure 17:
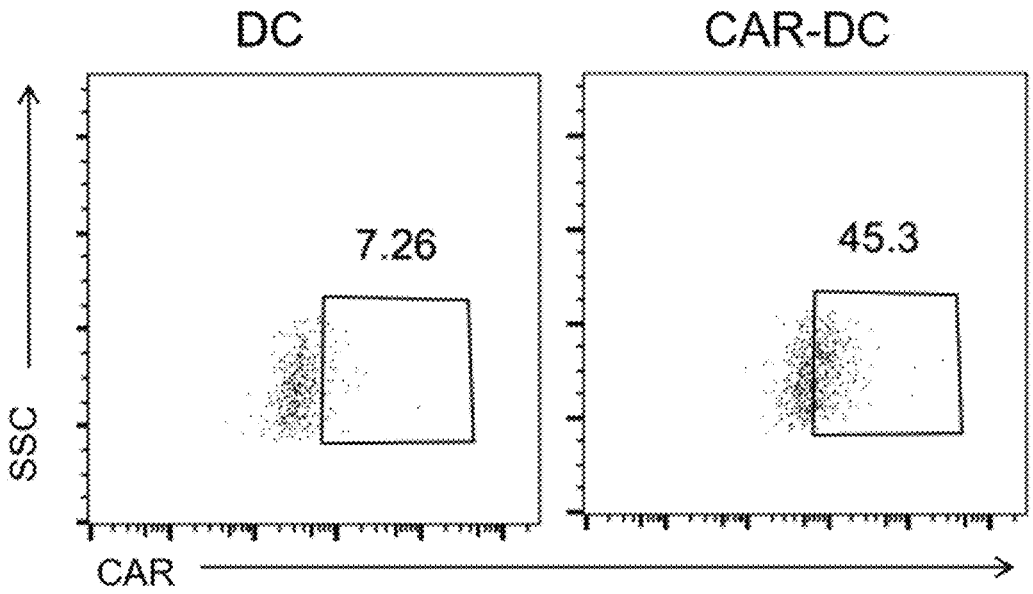
FIG. 17 shows the expression of CAR on a surface of humanized mouse bone marrow-derived DCs that is detected by flow cytometry.

9 lentivirus encoding a human CAR-DC receptor (the amino acid sequence of the human Epha2 CAR protein was set forth in SEQ ID NO: 21). 48 h later, a CAR expression efficiency was detected with protein L. As shown in FIG. 17, a transfection efficiency of CAR in DCs was 45.3%.

Figure 18:
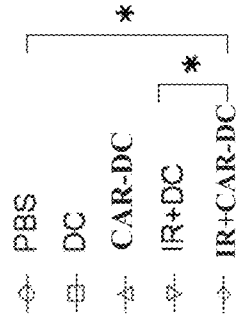
FIG. 18 shows tumor growth curves when human breast cancer SKRBR3 is treated with a combination of CAR-DC and radiotherapy.
Figure 18:
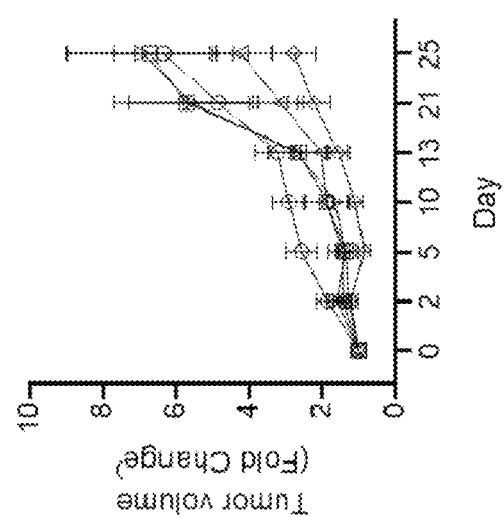

In vivo treatment: Human breast cancer cells SK-BR3 were transplanted into the humanized mice. One week after the tumor transplantation, the mice were randomly divided into the following five groups: a control group (PBS), a DC group, a CAR-DC group, a radiotherapy+DC group (IR+DC), and a radiotherapy+CAR-DC group (IR+CAR-DC). On day 2, mice in the radiotherapy+DC group and the radiotherapy+CAR-DC group each were subjected to X-ray irradiation at an irradiation dose of 1 Gy. On day 4, DCs and CAR-DCs each were infused through the tail vein at a dose of $3 \times 10^6$ cells/mouse. The growth of mouse tumors were continuously observed. A length and width of a tumor were measured regularly with an electronic vernier caliper. A volume of the tumor was calculated based on the length and width of the tumor according to the following calculation formula: (width^2*length)/2. A tumor volume of each measurement was determined with a measurement on day 0 as a baseline. A baselined tumor growth curve (calculation formula: $\text{Vol}_{Dayn}/\text{Vol}_{Day0}$) was plotted with the Prism Graphad software. It could be seen from tumor growth curves (FIG. 18) that the combination of the CAR-DC and the radiotherapy had a significant inhibitory effect on the growth of breast cancer (differences among groups were determined by t-test, *p<0.05).

The sequences involved in the present application include the following:

```
Amino acid sequence for mouse Epha2 CAR
(SEQ ID NO: 1):
MASPLTRFLSLNLLLLGESIILGSGEADIQMTQSPSSLSASVGDRVTIT
CRASQYYSYYGVAWYQQKPGKAPKLLIYGASYLYSGVPSRFSGSRSGTD
FTLTISSLQPEDFATYYCQQSFYPITFGQGTKVEIKGGGGSGGGGSGGG
GSEVQLVESGGGLVQPGGSLRLSCAASGFNLSGGGVHWVRQAPGKGLEW
VAGIYSSSGYTYYADSVKGRFTISADTSKNTAYLQMNSLRAEDTAVYYC
ARSSGGFDYWGQGTLVTVSSTTTKPVLRTPSPVHPTGTSQPQRPEDCRP
RGSVKGTGLDFACDIYIWAPLAGICVALLLSLIITLICYHRSRGVAIPR
WPSSPAQSGKESGRPRKHIDQTSFDLQTYGDEDLNEIHSHYKMRLKIQV
RKAAIASREKADAVYTGLNTRSQETYETLKHEKPPQ.

Nucleotide sequence for mouse Epha2 CAR
(SEQ ID NO: 2):
ATGGCCAGCCCTCTGACCAGATTCCTGTCTCTGAACCTGCTCCTGCTGG
GAGAGTCTATCATCCTGGGATCAGGAGAGGCTGACATCCAGATGACCCA
GAGCCCTTCCTCACTGAGCGCTTCCGTGGGTGACAGAGTGACTATTACC
TGCAGAGCCAGCCAGTACTACAGCTACTATGGAGTGGCCTGGTACCAGC
AGAAGCCTGGCAAAGCTCCTAAGCTGCTGATCTATGGAGCTTCTTACCT
GTACTCCGGGGTCCCATCTAGGTTCAGCGGCTCTAGGTCTGGCACCGAC
TTCACTCTGACCATCTCCAGCCTGCAGCCAGAAGACTTCGCCACCTACT
ACTGCCAGCAGAGTTTCTACCCCATCACCTTCGGACAGGGAACCAAGGT
GGAAATCAAAGGCGGCGGCGGGAGCGGGGGCGGCGGCTCTGGAGGCGGC
GGGTCCGAAGTCCAGCTGGTGGAGAGCGGCGGAGGTCTGGTGCAGCCAG
GCGGCTCCCTGAGACTGTCCTGCGCCGCCTCCGGCTTCAACCTGTCCGG
GGGTGGAGTGCACTGGGTGAGGCAGGCTCCCGGCAAGGGACTGGAGTGG
GTGGCTGGAATCTACTCCAGCTCCGGATACACATACTATGCCGACAGCG
TGAAGGGCAGGTTTACCATCAGCGCCGACACCTCTAAAAACACCGCATA
CCTGCAGATGAATAGCCTGCGAGCCGAGGATACAGCCGTGTATTACTGC
GCCAGGAGCTCCGGCGGCTTTGATTACTGGGGGCAGGGCACTCTGGTGA
CTGTGTCCTCTACAACAACTAAGCCTGTGCTGAGGACCCCTTCCCCTGT
GCACCCAACCGGCACCAGCCAGCCCCAGCGACCTGAGGACTGCAGACCC
CGGGGATCTGTGAAGGGCACCGGGCTGGATTTTGCATGTGACATTTATA
TCTGGGCCCCTCTGGCCGGCATCTGCGTGGCCCTGCTGCTGTCTCTGAT
CATTACCCTGATCTGCTATCATAGATCCAGAGGGGTGGCTATCCCCAGA
TGGCCTAGCAGCCCAGCCCAGAGTGGAAAAGAGAGCGGCCGCCCTAGAA
AGCACATCGACCAGACCTCTTTTGATCTGCAAACTTACGGTGACGAGGA
TCTGAATGAGATCCACTCTCACTACAAGATGAGGCTGAAGATACAGGTG
CGGAAGGCAGCCATCGCAAGCAGAGAGAAGGCCGACGCCGTGTACACAG
GCCTGAACACAAGATCTCAGGAGACCTATGAGACCCTGAAGCATGAGAA
GCCCCCCCAGTGA.
```

10

```
Amino acid sequence for the guide sequence of
mouse Epha2 CAR (SEQ ID NO: 3):
MASPLTRFLSLNLLLLGESIILGSGEA.

Nucleotide sequence for the guide sequence of
mouse Epha2 CAR (SEQ ID NO: 4):
ATGGCCAGCCCTCTGACCAGATTCCTGTCTCTGAACCTGCTCCTGCTGG
GAGAGTCTATCATCCTGGGATCAGGAGAGGCT.

Amino acid sequence for anti-mouse Epha2 VH
(SEQ ID NO: 5):
DIQMTQSPSSLSASVGDRVTITCRASQYYSYYGVAWYQQKPGKAPKLLI
YGASYLYSGVPSRFSGSRSGTDFTLTISSLQPEDFATYYCQQSFYPITF
GQGTKVEIK.

Nucleotide sequence for anti-mouse Epha2 VH
(SEQ ID NO: 6):
GACATCCAGATGACCCAGAGCCCTTCCTCACTGAGCGCTTCCGTGGGTG
ACAGAGTGACTATTACCTGCAGAGCCAGCCAGTACTACAGCTACTATGG
AGTGGCCTGGTACCAGCAGAAGCCTGGCAAAGCTCCTAAGCTGCTGATC
TATGGAGCTTCTTACCTGTACTCCGGGGTCCCATCTAGGTTCAGCGGCT
CTAGGTCTGGCACCGACTTCACTCTGACCATCTCCAGCCTGCAGCCAGA
AGACTTCGCCACCTACTACTGCCAGCAGAGTTTCTACCCCATCACCTTC
GGACAGGGAACCAAGGTGGAAATCAAA.

Amino acid sequence for anti-mouse Epha2 VL
(SEQ ID NO: 7):
EVQLVESGGGLVQPGGSLRLSCAASGFNLSGGGVHWVRQAPGKGLEWVA
GIYSSSGYTYYADSVKGRFTISADTSKNTAYLQMNSLRAEDTAVYYCAR
SSGGFDYWGQGTLVTVSS.

Nucleotide sequence for anti-mouse Epha2 VL
(SEQ ID NO: 8):
GAAGTCCAGCTGGTGGAGAGCGGCGGAGGTCTGGTGCAGCCAGGCGGCT
CCCTGAGACTGTCCTGCGCCGCCTCCGGCTTCAACCTGTCCGGGGGTGG
AGTGCACTGGGTGAGGCAGGCTCCCGGCAAGGGACTGGAGTGGGTGGCT
GGAATCTACTCCAGCTCCGGATACACATACTATGCCGACAGCGTGAAGG
GCAGGTTTACCATCAGCGCCGACACCTCTAAAAACACCGCATACCTGCA
GATGAATAGCCTGCGAGCCGAGGATACAGCCGTGTATTACTGCGCCAGG
AGCTCCGGCGGCTTTGATTACTGGGGGCAGGGCACTCTGGTGACTGTGT
CCTCT.

Amino acid sequence for the linker of mouse Epha2
CAR (SEQ ID NO: 9):
GGGGSGGGGSGGGGS.

Nucleotide sequence for the linker of mouse Epha2
CAR (SEQ ID NO: 10):
GGCGGCGGCGGGAGCGGGGGCGGCGGCTCTGGAGGCGGCGGGTCC.

Amino acid sequence for the CD8a hinge domain of
the mouse (SEQ ID NO: 11):
TTTKPVLRT PSPVHPTGTS QPQRPEDCRPRGSVKGTGLD FACDIY.

Nucleotide sequence for the CD8a hinge domain of
the mouse (SEQ ID NO: 12):
ACAACAACTAAGCCTGTGCTGAGGACCCCTTCCCCTGTGCACCCAACCG
GCACCAGCCAGCCCCAGCGACCTGAGGACTGCAGACCCCGGGGATCTGT
GAAGGGCACCGGGCTGGATTTTGCATGTGACATTTAT.

Amino acid sequence for the CD8a transmembrane
domain of the mouse (SEQ ID NO: 13):
IWAPLAGICVALLLSLIITLICYHRSR.

Nucleotide sequence for the CD8a transmembrane
domain of the mouse (SEQ ID NO: 14):
ATCTGGGCCCCTCTGGCCGGCATCTGCGTGGCCCTGCTGCTGTCTCTGA
TCATTACCCTGATCTGCTATCATAGATCCAGA.

Amino acid sequence for the Dectin1 intracellular
domain of the mouse (SEQ ID NO: 15):
GVAIPRWPSSPAQSGKESGRPRKHIDQTSFDLQTYGDEDLNEIHSHYKM.

Nucleotide sequence for the Dectin1 intracellular
domain of the mouse (SEQ ID NO: 16):
GGGGTGGCTATCCCCAGATGGCCTAGCAGCCCAGCCCAGAGTGGAAAAG
AGAGCGGCCGCCCTAGAAAGCACATCGACCAGACCTCTTTTGATCTGCA
AACTTACGGTGACGAGGATCTGAATGAGATCCACTCTCACTACAAGATG.
```

-continued

Amino acid sequence for the intracellular domain
of mouse FcR gamma (SEQ ID NO: 17):
RLKIQVRKAAIASREKADAVYTGLNTRSQETYETLKHEKPPQ.

Nucleotide sequence for the intracellular domain
of mouse FcR gamma (SEQ ID NO: 18):
AGGCTGAAGATACAGGTGCGGAAGGCAGCCATCGCAAGCAGAGAGAAGG
CCGACGCCGTGTACACAGGCCTGAACACAAGATCTCAGGAGACCTATGA
GACCCTGAAGCATGAGAAGCCCCCCCAG.

Forward strand of the primer for mouse CAR IVT
(in vitro transcription) (SEQ ID NO: 19):
ATAATACGACTCACTATAGGGAGAGCCACCATGGCCAGCCCTCTGACCA
G.

Reverse strand of the primer for mouse CAR IVT
(SEQ ID NO: 20):
TTTTTTTTTTTTTTCTGTCTTTTTATTGCCGTCACTGGGGGGGCTTCTCA
T.

-continued

Amino acid sequence for human Epha2 CAR
(SEQ ID NO: 21):
MALPVTALLLPLALLLHAARPQVQLLESGGGLVQPGGSLRLSCAASGFT
FSSYTMSWVRQAPGQALEWMGTISSRGTYTYYPDSVKGRFTISRDNAKN
SLYLQMNSLRAEDTAVYYCAREAIFTHWGRGTLVTVSSGGGGSGGGGSG
GGGSDIQLTQSPSSLSASVGDRVTITCKASQDINNYHSWYQQKPGQAPR
LLIYRANRLVDGVPDRESGSGYGTDFTLTINNIESEDAAYYFCLKYNVF
PYTFGQGTKVEIKTTTPAPRPPTPAPTIASQPLSLRPEACRPAAGGAVH
TRGLDFACDIYIWAPLAGTCGVLLLSLVITLYCRWPPSAACSGKESVVA
IRTNSQSDFHLQTYGDEDLNELDPHYEMRLKIQVRKAAITSYEKSDGVY
TGLSTRNQETYETLKHEKPPQ.

Finally, it should be noted that the above examples are provided merely to describe the technical solutions of the present application, rather than to limit the protection scope of the present application. Although the present application is described in detail with reference to preferred examples, a person of ordinary skill in the art should understand that modifications or equivalent replacements may be made to the technical solutions of the present application without departing from the spirit and scope of the technical solutions of the present application.

The invention claimed is:

1. A chimeric antigen receptor (CAR), wherein the CAR has an amino acid sequence set forth in SEQ ID NO: 1.

2. A nucleic acid encoding the CAR according to claim 1, wherein the nucleic acid has a nucleotide sequence set forth in SEQ ID NO: 2.

3. An engineered dendritic cell (DC) comprising the CAR according to claim 1.

4. An engineered DC comprising a nucleic acid encoding the CAR according to claim 2.

5. The engineered DC according to claim 3, wherein the engineered DC is derived from at least one selected from the group consisting of a peripheral blood mononuclear cell, a hematopoietic stem cell, an induced pluripotent stem cell, and an embryonic stem cell.

6. A preparation method of an engineered DC, comprising the following steps: transforming DNA or mRNA encoding the CAR according to claim 1 into a DC, and allowing for expression.

7. The preparation method of an engineered DC according to claim 6, wherein the DNA or mRNA encoding the CAR is comprised in any one selected from the group consisting of an expression plasmid, a lentivirus, and a liposome.

8. A preparation comprising an engineered DC comprising the CAR according to claim 1.

9. A drug or preparation comprising the engineered DC according to claim 3, a pharmaceutically acceptable adjuvant, and/or a carrier or an excipient acceptable in a preparation process.

10. A method for treating a tumor, comprising: administering a population of engineered DCs modified with the CAR according to claim 1 to a tumor patient in combination with radiotherapy.

11. The method for treating a tumor according to claim 10, wherein the radiotherapy comprises external beam radiation therapy and/or intracavitary radiotherapy.

12. The method for treating a tumor according to claim 11, wherein the external beam radiation therapy comprises at least one selected from the group consisting of an X-knife, a gamma knife, and a linear accelerator; and the intracavitary radiotherapy comprises seed implantation.

13. The method for treating a tumor according to claim 10, wherein the tumor comprises any one selected from the group consisting of breast cancer, lung cancer, colorectal cancer, liver cancer, pancreatic cancer, melanoma, glioma, ovarian cancer, and prostate cancer.

* * * * *